United States Patent
Ninh

(10) Patent No.: US 11,801,077 B2
(45) Date of Patent: Oct. 31, 2023

(54) BONE FIXATION SYSTEM

(71) Applicant: Christopher Ninh, Irvine, CA (US)

(72) Inventor: Christopher Ninh, Irvine, CA (US)

(73) Assignee: Orthotek, LLC., Los Alamitos, CA (US)

( * ) Notice: Subject to any disclaimer, the term of this patent is extended or adjusted under 35 U.S.C. 154(b) by 0 days.

(21) Appl. No.: 17/694,484

(22) Filed: Mar. 14, 2022

(65) Prior Publication Data

US 2023/0285057 A1    Sep. 14, 2023

(51) Int. Cl.
| A61B 17/72 | (2006.01) |
| A61B 17/86 | (2006.01) |
| A61B 17/84 | (2006.01) |

(52) U.S. Cl.
CPC .......... *A61B 17/725* (2013.01); *A61B 17/846* (2013.01); *A61B 17/863* (2013.01)

(58) Field of Classification Search
CPC .... A61B 17/725; A61B 17/846; A61B 17/863
USPC ...................................... 606/62–68
See application file for complete search history.

(56) References Cited

U.S. PATENT DOCUMENTS

| 5,032,125 A * | 7/1991 | Durham .............. A61B 17/744 606/65 |
| 6,443,954 B1 | 9/2002 | Bramlet et al. |
| 8,449,544 B2 * | 5/2013 | Grusin ............... A61B 17/7283 606/64 |
| 9,204,910 B2 | 12/2015 | Epperly |
| 10,758,281 B2 | 9/2020 | Hansson |
| 2002/0032445 A1 | 3/2002 | Fujiwara |
| 2005/0055024 A1 * | 3/2005 | James ................ A61B 17/1668 606/64 |
| 2006/2001160 | 9/2006 | Border et al. |
| 2007/0270848 A1 * | 11/2007 | Lin ...................... A61B 17/746 606/65 |
| 2018/0078299 A1 * | 3/2018 | Rossney ............. A61B 17/725 |
| 2020/0305937 A1 | 10/2020 | Yacoubian |

OTHER PUBLICATIONS

Moor, BK, et al.,Distal locking of femoral nails. Mathematical analysis of the appropriate targeting range. ORTHOP TRAUMATOL-SUR 2012; 98:85-89. Downloaded from https://www.sciencedirect.com/science/article/pii/S1877056811002805?via%3Dihub on Jan. 24, 2022.

(Continued)

*Primary Examiner* — Eduardo C Robert
*Assistant Examiner* — Tara Rose E Carter
(74) *Attorney, Agent, or Firm* — Roland Tong

(57) ABSTRACT

A bone fixation system includes an intramedullary nail and a lag screw. A proximal portion of the intramedullary nail includes a first proximal bore configured to accept the lag screw and a second proximal bore configured to accept a portion of an antirotation screw insertion tool. A distal portion of the intramedullary nail defines at least one opening configured to accept a distal locking screw. The lag screw includes a sheath and a rod mounted for sliding movement within the sheath. The rod has a threaded distal end defining a diagonal bore configured to accept an antirotation screw.

10 Claims, 6 Drawing Sheets

(56) References Cited

OTHER PUBLICATIONS

Gazzotti, G, et al. Causes and treatments of lag screw's cut out after intramedullary nailing osteosinthesis for trochanteric fractures. Acta Biomed 2014; 85, N.2:135-143. Downloaded on Jan. 11, 2022.

Buruian, B, et al. Distal interlocking for short trochanteric nails: static, dynamic or no locking? Review of the literature and decision algorithm. EFORT Open Rev 2020;5:421-429. Downloaded from https://www.ncbi.nlm.nih.gov/pmc/articles/PMC7407850/ on Jan. 24, 2022.

Double Medical. Proximal femoral bionic nail. Downloaded from https://www.doublemedicalgp.com/proximal-femoral-bionic-nail_p206.html on Feb. 15, 2022.

Wright, RC, et al. The extended-short nail system, a novel concept in the management of proximal femur fractures. Am J Orthop 2011;40(12):630-635. Downloaded from https://cdn.mdedge.com/files/s3fs-public/Document/September-2017/040120630.pdf on Jan. 24, 2022.

Stryker Medical Education.Gamma3® Long Nail R1.5 and R2.0 Operative Technique. Downloaded from https://www.strykermeded.com/media/1310/gamma3-long-nail-r15-and-r20-operative-technique.pdf on Feb. 15, 2022.

Advanced Orthopaedic Solutions. AOS Galileo® Trochanteric Nail System: instructions for use. Downloaded from https://www.arthrex.com/resources/instructions-for-use/n1UWST716k2-_QF8TC6RjQ/aos-advanced-orthopaedic-solutions on Jan. 24, 2022.

Zhu, Y, et al. Is the lag screw sliding effective in the intramedullary nailing in A1 and A2 AO-OTA intratrochanteric fractures? A prospective study of sliding and none-sliding lag screw in Gamma-III nail. Scand J Trauma Resuc Emerg 2012; 20:60. Downloaded from https://sjtrem.biomedcentral.com/articles/10.1186/1757-7241-20-60 on Jan. 24, 2022.

Jagow, DM, et al. A novel technique for the fixation of intertrochanteric hip fractures: a telescoping lag screw. J Orthop 2018;15(2):690-694. Downloaded from https://www.ncbi.nlm.nih.gov/pmc/articles/PMC5990323 on Jan. 10, 2022.

Li, Y-H et al. Distal locked versus unlocked intramedullary nailing for stable intertrochanteric fractures, a systematic review and meta-analysis. BMC musculoskeletal disorders 2020;21:461. Downloaded from https://bmcmusculoskeletdisord.biomedcentral.com/articles/10.1186/s12891-020-03444-6 on Jan. 24, 2022.

Vopat, BG, et al. Is distal locking of long nails for intertrochanteric fractures necessary? A clinical study. J Clin Orthop Trauma 2014: 233-239 Downloaded from https://www.ncbi.nlm.nih.gov/pmc/articles/PMC4264043/ on Jan. 24, 2022.

Jagow, DM, et al. Efficacy of the AOS Galileo™ telescoping lag screw for the treatment of intertrochanteric hip fractures. Downloaded from https://static1.squarespace.com/static/5afa06548ab7228349a8a2a7/t/5b89641870a6ad36f883b8a8/1535730713745/White+Paper+-+Galileo+Lag+Screw+Study.pdf on Jan. 10, 2022.

Zhang, Y, et al. Long and short intramedullary nails for fixation of intertrohanteric femur fractures (OTA 31-A1, A2 and A3): A systematic review and meta-analysis. Orthop Traumatol Surg Res 2017; 103:685-690. Downloaded from https://www.sciencedirect.com/science/article/pii/S1877056817301366 on Jan. 7, 2022.

Orthofix, Operative Technique: Vero™ Nail Trochanteric System. Downloaded from https://www.orthofix.com/wp-content/uploads/2019/01/VN-0702-OPT-E0.pdf on Mar. 14, 2022.

* cited by examiner

BONE FIXATION SYSTEM

BACKGROUND OF THE INVENTION

1. Field of the Invention

The present disclosure relates in general to bone fixation devices and, more particularly, to an intramedullary nail with a lag screw.

2. Background Art

Hip fractures have become increasingly common over the years, as the American population ages. One of the most prevalent types of hip fracture is the intertrochanteric fracture, which consists of a break between the greater and lesser trochanters of the femur. Such fractures are frequently repaired using a metal rod that is inserted through the proximal end of the femur and into the medullary cavity of the femoral shaft. This rod, called an intramedullary nail, may be locked in place at its distal end with one or more cortical screws, and at its proximal end with a cephalic lag screw that extends diagonally through the nail, across the fracture, and into the femoral head. The lag screw compresses the separated parts of the femur against one another, allowing healing to occur. Typically, the lag screw is secured to the nail by a set screw inserted through a threaded hole in the nail.

One problem associated with intramedullary nails is a tendency for the separated portion of the bone to rotate about the lag screw, which can delay healing and, in extreme cases, damage the muscle surrounding the femoral head. Some fixation systems address this problem by extending an auxiliary cephalic screw, sometimes called an antirotation screw, through the proximal end of the nail. In most systems, the auxiliary screw extends parallel to the lag screw, although in one commercially available system for use in subtrochanteric fractures, an auxiliary screw converges with the lag screw.

Lag screws can either be fixed or slidable with respect to the intramedullary nail. Repairs utilizing fixed lag screws sometimes fail due to a problem called "cut-out", wherein the threaded end of the lag screw pierces the femoral head cortex and projects into the patient's pelvis. On the other hand, repairs utilizing sliding lag screws may fail due to lateral lag screw protrusion, wherein fracture settlement causes the lag screw to protrude laterally into the surrounding soft tissues, often leading to significant lateral thigh pain. In systems including two parallel lag screws, the two screws may move in opposite directions, causing both cut-out and lateral protrusion to occur—a phenomenon known as the "Z-effect."

In addition to choosing between intramedullary nails with fixed lag screws and those with sliding lag screws, a surgeon needs to select either a long or a short intramedullary nail, with or without distal fixation. Long nails have greater rotational rigidity and result in a lower rate of peri-prosthetic fracture than short nails, but distal locking of long nails is difficult and requires extensive use of fluoroscopy to locate the locking screws. The use of fluoroscopy increases the amount of time the surgeon and operative team are exposed to radiation, and in addition, increases the operating time and overall cost of the operation. For this reason, many surgeons use long nails without distal fixation for stable fractures, although distal fixation is still advisable for unstable fractures.

In recent years, a hybrid "extended short" nail has become available. The extended short nail has the same length as a conventional long nail (typically in the range of 30 to 45 cm for adults), but is locked at the same location as a conventional short nail, thus combining the mechanical properties of a conventional long nail with the ease of use of a conventional short nail. Locking openings are also provided at the distal end of the extended short nail for use in unstable fractures or other special circumstances. However, use of the distal openings in extended short nails requires extensive fluoroscopy, just as in conventional long nails.

These and other problems are addressed by this disclosure as summarized below.

SUMMARY OF THE INVENTION

In one aspect of the present disclosure, a bone fixation system includes an intramedullary nail and a lag screw. A proximal portion of the intramedullary nail includes a first proximal bore configured to accept the lag screw and a second proximal bore configured to accept a portion of an antirotation screw insertion tool. A distal portion of the intramedullary nail defines at least one opening configured to accept a distal locking screw. The lag screw includes a sheath and a rod mounted for sliding movement within the sheath. The rod has a threaded distal end defining a diagonal bore configured to accept an antirotation screw.

In another aspect of the disclosure, the first proximal bore extends at an angle in the range of about 120° to about 140° with respect to the longitudinal axis of the distal portion of the intramedullary nail, and the second proximal bore extends at an angle in the range of about 90° and about 105° with respect to the longitudinal axis of the distal portion of the intramedullary nail.

In another aspect of the disclosure, the bone fixation system also includes an antirotation screw configured to be inserted through the diagonal bore in the threaded distal end of the rod, and a locking mechanism configured to lock the antirotation screw within the diagonal bore.

In yet another aspect of the disclosure, the locking mechanism comprises mating threads on the proximal end of the antirotation screw and inside the diagonal bore.

In still another aspect of the disclosure, the rod of the lag screw has a longitudinal axis, and the diagonal bore extends at an angle in the range of about 25° to about 55° with respect to the longitudinal axis of the rod.

In yet still another aspect of the disclosure, the sheath of the lag screw has a predetermined outer diameter, and the antirotation screw has a predetermined diameter not more than half the predetermined outer diameter of the sheath of the lag screw.

In another aspect of the disclosure, the lag screw has a predetermined length when fully extended, and the antirotation screw has a predetermined length no more than ¾ths of the predetermined length of the lag screw.

In another aspect of the disclosure, a method of repairing a fracture comprises implanting an intramedullary nail in a femur, inserting a telescoping lag screw through a first proximal bore in a proximal portion of the intramedullary nail, mounting an antirotation screw at the end of an antirotation screw insertion tool, passing the antirotation screw insertion tool through a second proximal bore in the proximal portion of the intramedullary nail, manipulating the antirotation screw insertion tool to lock the antirotation screw within a diagonal bore through the threaded distal end of the telescoping lag screw, and removing the antirotation screw insertion tool.

In still another aspect of the disclosure, the intramedullary nail has a proximal end and a predetermined length. The distal portion of the intramedullary nail defines a targeted screw hole located a predetermined distance from the proximal end of the intramedullary nail, wherein the predetermined distance is between about 44% and about 67% of the predetermined length of the nail.

In yet another aspect of the disclosure, the intramedullary nail has a proximal end, a distal tip, and a predetermined length. The distal portion of the intramedullary nail defines a first targeted screw, a distal locking hole located near the distal tip of the intramedullary nail, a distal locking slot located in close proximity to the distal locking hole, and a second targeted screw hole located between the first targeted screw hole and the distal locking hole. The first targeted screw hole is located a first predetermined distance away from the proximal end of the intramedullary nail, wherein the first predetermined distance is between about 34% and about 52% of the predetermined length of the intramedullary nail. The second targeted screw hole is located between the first targeted screw hole and the distal locking hole.

In another aspect of the disclosure, a lag screw for proximally locking an intramedullary nail in a bone includes a sheath and a rod mounted for sliding movement within the sheath. The rod includes a threaded distal end defining a diagonal bore configured to accept an antirotation screw.

In still another aspect of the disclosure, the rod of the lag screw has a longitudinal axis, and the diagonal bore extends at an angle in the range of about 25° to about 55° with respect to the longitudinal axis of the rod.

In yet another aspect of the disclosure, a bone fixation system includes a telescoping lag screw having a diagonal bore extending through its threaded distal end, an antirotation screw configured to be inserted through the diagonal bore in the threaded distal end of the rod, and a locking mechanism configured to lock the antirotation screw within the diagonal bore.

In still another aspect of the disclosure, an intramedullary nail has a proximal end, a distal portion terminating in a distal tip, and a predetermined length. The distal portion defines a first targeted screw hole, a distal locking screw located near the distal tip of the intramedullary nail, a distal locking slot located near the distal locking hole, and a second targeted screw hole located between the first targeted screw hole and the distal locking hole. The first targeted screw hole is located a first predetermined distance away from the proximal end of the intramedullary nail, wherein the first predetermined distance is between about 34% and about 52% of the predetermined length of the intramedullary nail.

In another aspect of the disclosure, the second targeted screw hole is located a predetermined distance from the proximal end of the intramedullary nail, wherein the predetermined distance is between about 44% and about 67% of the predetermined length of the nail.

DETAILED DESCRIPTION OF THE PREFERRED EMBODIMENT(S)

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
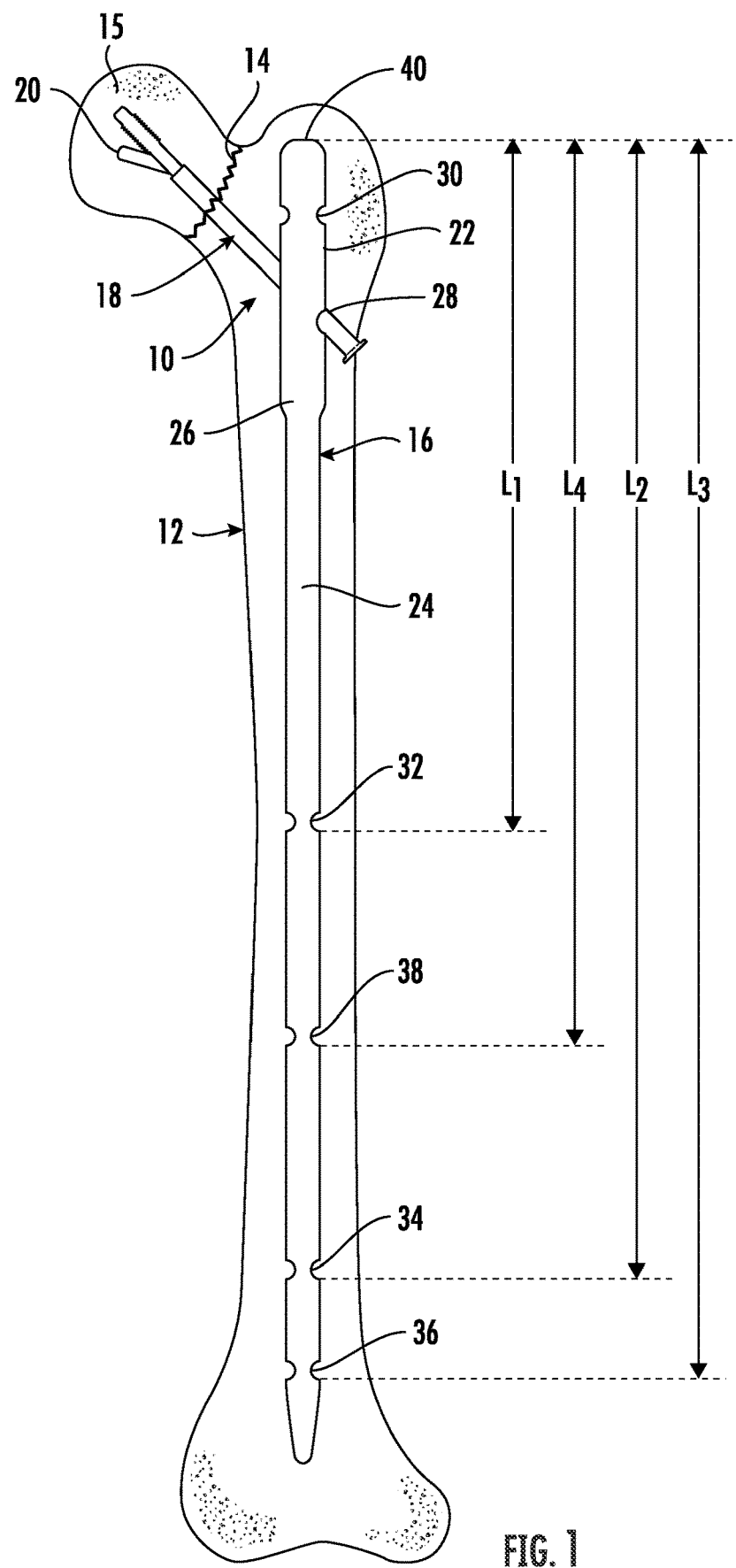
FIG. 1 shows an intramedullary fixation system within a femur.

FIG. 1 shows a bone fixation system according to the present disclosure, indicated in its entirety by the numeral 10, located in a femur 12 having a fracture 14. The illustrated fracture is intertrochanteric; however, the bone fixation system 10 may also be used for a variety of other types of fractures including basicervical and subtrochanteric. The bone fixation system 10 includes an intramedullary nail 16, a lag screw 18, and an antirotation screw 20.

The intramedullary nail 16, which may made from stainless steel, titanium alloy, or similar material, includes a proximal portion 22 and a distal portion 24 joined at a curved or bent portion 26 giving the nail 16 a slight anterior bow. For adults, the length of the intramedullary nail 16 may be between about 30 and about 45 cm, with a proximal bend of about 5°. The proximal portion 22 includes a first proximal bore 28 for accepting the lag screw 18, and a second proximal bore 30 for accepting a portion of an antirotation screw insertion tool, as will be described later. The first proximal bore 28 is oriented in an angular direction toward the tip of the femoral head 15. In a typical example, the angle between the longitudinal axis of the first proximal bore 28 and the longitudinal axis of the distal portion 24 of the intramedullary nail 16 will be between 120° and 140°, depending on the patient's anatomy. The first proximal bore 28 may have an anteversion of 10°. The second proximal bore 30 is oriented in an angular direction toward a location slightly proximal to and lateral of the center of the femoral head 15. In a typical example, the angle between the longitudinal axis of the second proximal bore 30 and the longitudinal axis of the distal portion 24 of the intramedullary nail 16 will be between about 90° and about 105° with respect to the longitudinal axis of the distal portion 24 of the intramedullary nail 16.

The distal portion 24 of the intramedullary nail 16 includes a first targeted screw hole 32, a distal locking hole 34, a distal locking slot 36 and a second targeted screw hole 38, all for receiving cortical screws. The first targeted screw hole 32 is located a distance $L_1$ from the proximal end 40 of the intramedullary nail 16, where $L_1$ is the same distance as the distance between the proximal end and the distal locking hole in a conventional short intramedullary nail—typically 155 mm, which is between about 34% and about 52% of the total length of the intramedullary nail. The distal locking hole 34 is located a distance $L_2$ from the proximal end 40 of the intramedullary nail 16—for example, in the range of 255 to 375 m. The distal slot 36, which is an oblong opening with a length of 5 mm, is located a distance $L_3$ from the proximal end of the intramedullary nail 16—for example, in the range of 280 to 400 mm. The second targeted screw hole 38 is located a distance $L_4$ from the proximal end 40 of the intramedullary nail 16—for example, 200 mm, which is between about 44% and 67% of the total length of the nail.

This arrangement of locking holes allows a surgeon to choose from a greater variety of distal locking options depending on factors such as the fracture pattern, the patient's anthropometry, and the surgeon's own preferences. In one example, for a stable fracture, the surgeon may choose to forego distal locking altogether. In another example, for an unstable fracture, the physician may create a static locking mechanism by placing a single screw in any of the holes, or by placing a first screw in either the first targeted screw hole 32, the second targeted screw hole 38, or the distal locking hole 34, and a second screw in either the second targeted hole 38, the distal locking hole 34, or the proximal portion of the distal locking slot 36. For a fracture that is length stable but rotationally unstable, the surgeon may choose to create a dynamic locking mechanism by placing a single screw through the distal end of the distal locking slot 36. In situations requiring secondary dynamization, the surgeon may place a first screw through the distal locking hole 34 and a second screw through the distal end of the distal locking slot 36, and then remove the first screw after a period of time.

An advantage of using one or both of the targeted screw holes 32, 38 rather than the distal locking hole 34 and/or distal locking slot 36 is that these can be placed using a targeting arm, with minimal use of fluoroscopy. Another advantage of providing two targeted screw holes is that it allows for more options in the event of periprosthetic fracture. For instance, if a patient having a single screw through the first targeted screw hole 32 sustains a periprosthetic fracture distal to the first targeted screw hole 32 and proximal to the second targeted screw hole 38, the surgeon may be able to manage the fracture by inserting a screw through the second targeted screw hole 38, without needing to extract hardware, and with minimal use of fluoroscopy.

Figure 2:
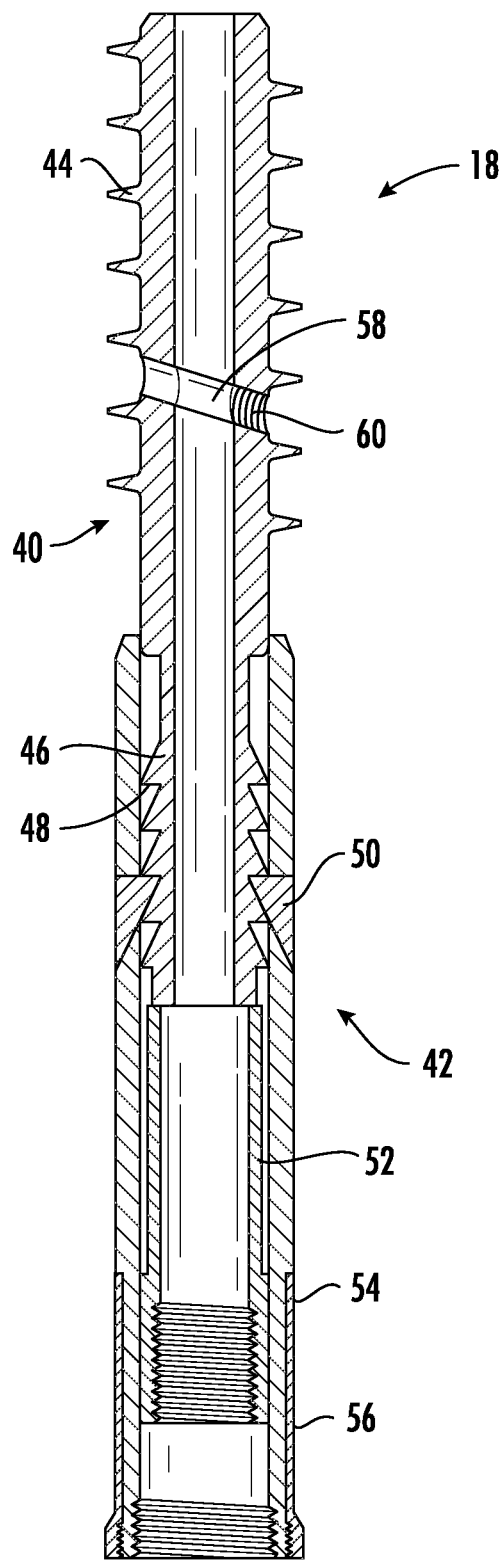
FIG. 2 shows a lag screw.

FIG. 2 is an enlarged sectional view of the lag screw 18, which includes a rod 40 mounted for sliding movement in a sheath 42. The sheath may have an outer diameter of about 10.5 mm, and the length of the lag screw 18 when fully extended may be about 120 mm. The distal portion 44 of the rod 40 is externally threaded and the proximal portion 46 of the rod 40 includes externally extending teeth 48 that cooperate with inwardly projecting teeth 50 coupled to the sheath 42 to create a ratchet mechanism ensuring that movement of the rod is unidirectional. An activation sleeve 52 prevents premature retraction of the rod 40. A locking mechanism such as an expandable locking ring 54 actuated by a sliding locking sleeve 56 may be provided for securing the lag screw 18 to the intramedullary nail. Alternatively, the lag screw 18 may be secured to the intramedullary nail by an externally applied set screw.

A diagonal bore 58 for receiving an antirotation screw extends through the threaded distal portion 44 of the rod 40, at an angle of about 25° to 55° with respect to the longitudinal axis of the rod 40. The proximal end 60 of the diagonal bore 58 is internally threaded.

Figure 3:
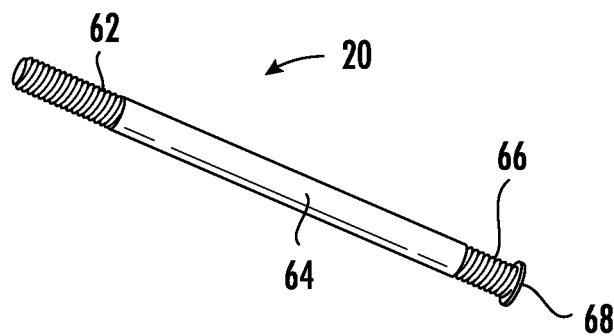
FIG. 3 shows an antirotation screw.

The antirotation screw 20, best shown in FIG. 3, includes a distal threaded portion 62 configured to achieve good purchase in the femoral head, a shank 64, a proximal threaded portion 66 and a screw head 68. When the antirotation screw 20 is inserted through the diagonal bore 58 in the lag screw 18, the distal end 62 projects laterally out of one side of the lag screw 18 and into the femoral head. The screw head 68 abuts the other side of the lag screw 18, preventing the antirotation screw 20 from being inserted too deeply into the femoral head, while the threads on the proximal threaded portion 66 engage the threads in the internally threaded proximal end 60 of the diagonal bore 58 of the lag screw 18, preventing the antirotation screw 20 from backing out. The antirotation screw 20 may have a diameter of about 5 mm and a length of about one half to three quarters the length of the lag screw 18.

Figure 4:
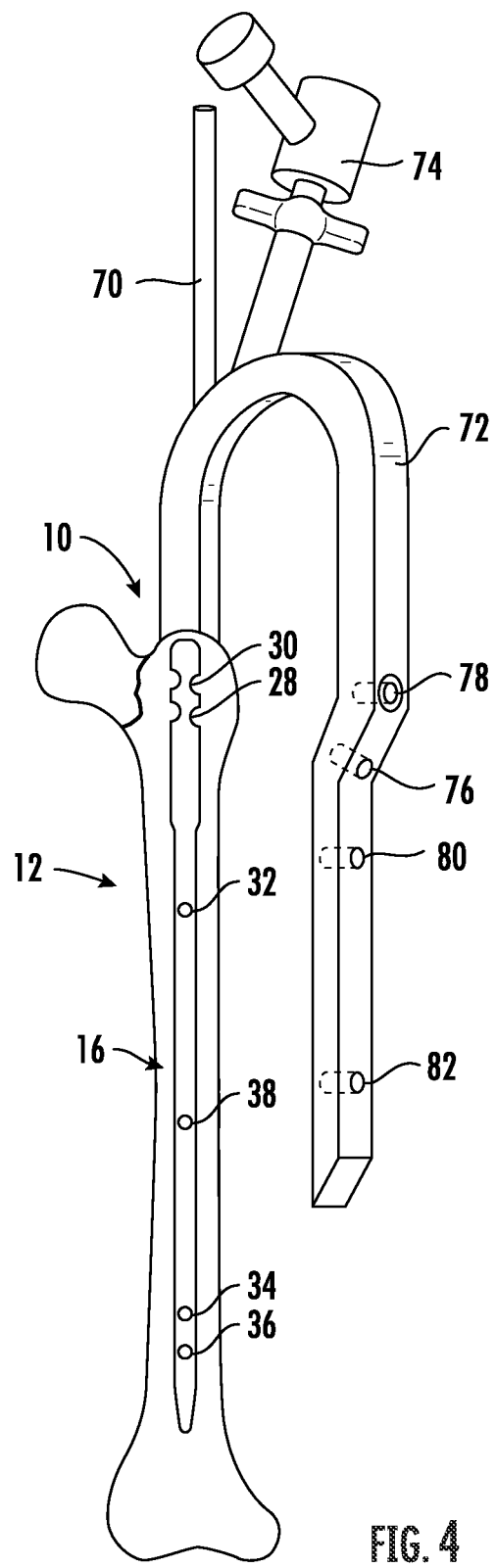
FIG. 4 shows an intramedullary nail being inserted into a femur.

FIGS. 4-8 illustrate steps of a bone fixation method using a bone fixation system 10 according to the present disclosure. Initially, access to the medullary canal of the patient's femur 12 is created through the greater trochanter using conventional methods. An intramedullary nail 16 is then introduced over a guidewire 70 using a radiolucent targeting arm 72, and the intramedullary nail 16 is gently hammered into place using a mallet 74, as shown in FIG. 4. The targeting arm 72 is longer than standard targeting arms and includes a lag screw targeting bore 76 configured to align with the first proximal bore 28 in the proximal portion 22 of the intramedullary nail 16, an antirotation screw targeting bore 78 configured to align with the second proximal bore 30 in the proximal portion 22 of the intramedullary nail 16, a proximal cortical screw targeting bore 80 configured to align with the first targeted screw hole 32 in the distal portion 24 of the intramedullary nail 16, and a distal cortical screw targeting bore 82 configured to align with the second targeted screw hole 38 in the distal portion 24 of the intramedullary nail 16.

Figure 5:
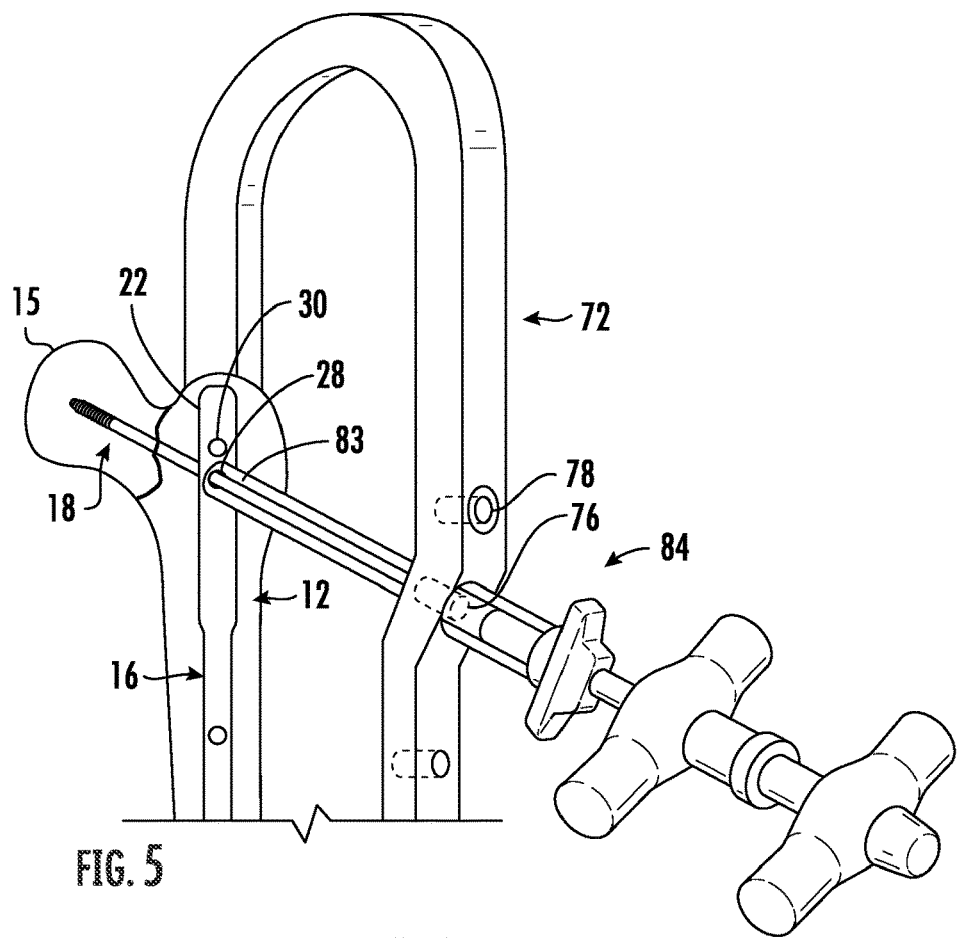
FIG. 5 shows a lag screw being inserted through an intramedullary nail in a femur.

After the intramedullary nail has been implanted, a drill is passed through the lag screw targeting bore 76 in the targeting arm, and actuated to create a lag screw passageway extending through the lateral cortex of the femur 12 and the first proximal bore 28 in the proximal portion 22 of the intramedullary nail 16. The drill is then withdrawn, and the lag screw 18 is inserted into the lag screw passageway 83 using a lag screw inserter assembly 84, as shown in FIG. 5. The lag screw inserter assembly 84 is rotated until the threaded distal end of the lag screw has reached a sufficient depth within the femoral head 15, and is then withdrawn, leaving the lag screw 18 in place. The activation sleeve is then removed from the lag screw 18, to allow for postoperative compression.

Figure 6:
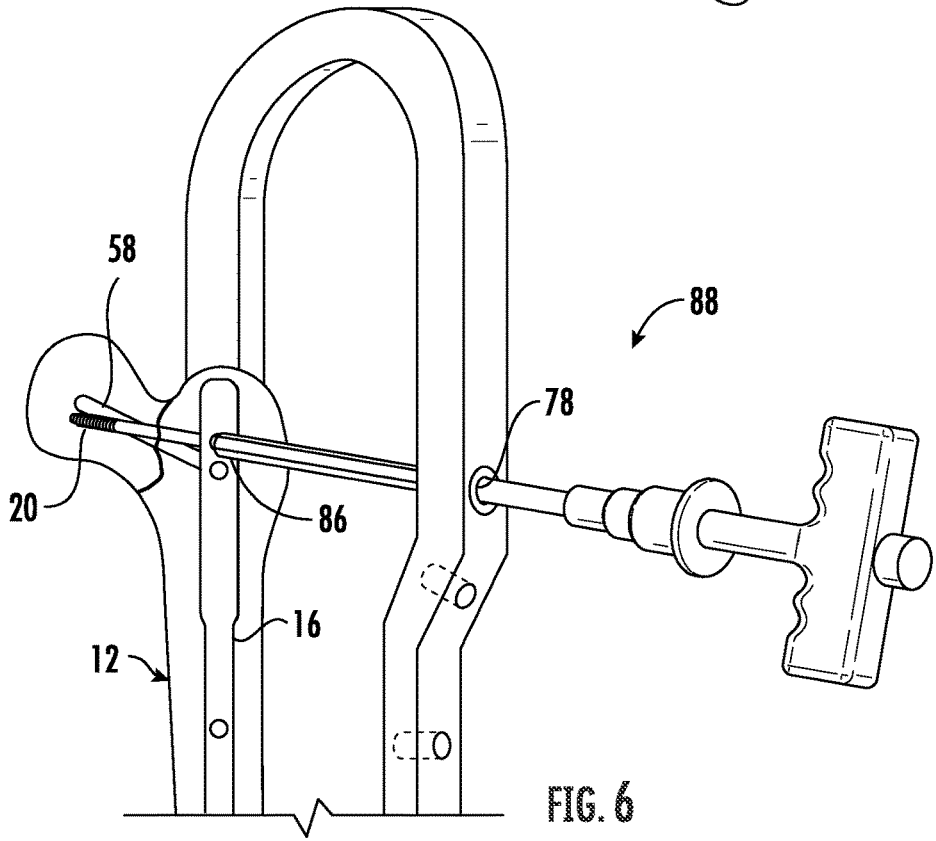
FIG. 6 shows an antirotation screw being inserted through a lag screw in a femur.

Next, a drill is passed through the antirotation screw targeting bore 78 in the targeting arm, and actuated to create an antirotation screw passageway extending through the lateral cortex of the femur 12, the second proximal bore 30 in the proximal portion 22 of the intramedullary nail 16, and the diagonal bore 58 in the slidable distal end of the lag screw 18. The drill is then withdrawn, and the antirotation screw 20 is inserted into the antirotation screw passageway 86 using a screwdriver 88, as shown in FIG. 6. The screwdriver 88 is rotated until the threads on the proximal threaded portion of the antirotation screw 20 engage the threads in the internally threaded proximal end of the diagonal bore 58 through the lag screw 18 and the head of the antirotation screw 20 abuts the side of the lag screw 18. The screwdriver 88 is then withdrawn, leaving the antirotation screw 20 in place.

Figure 7:
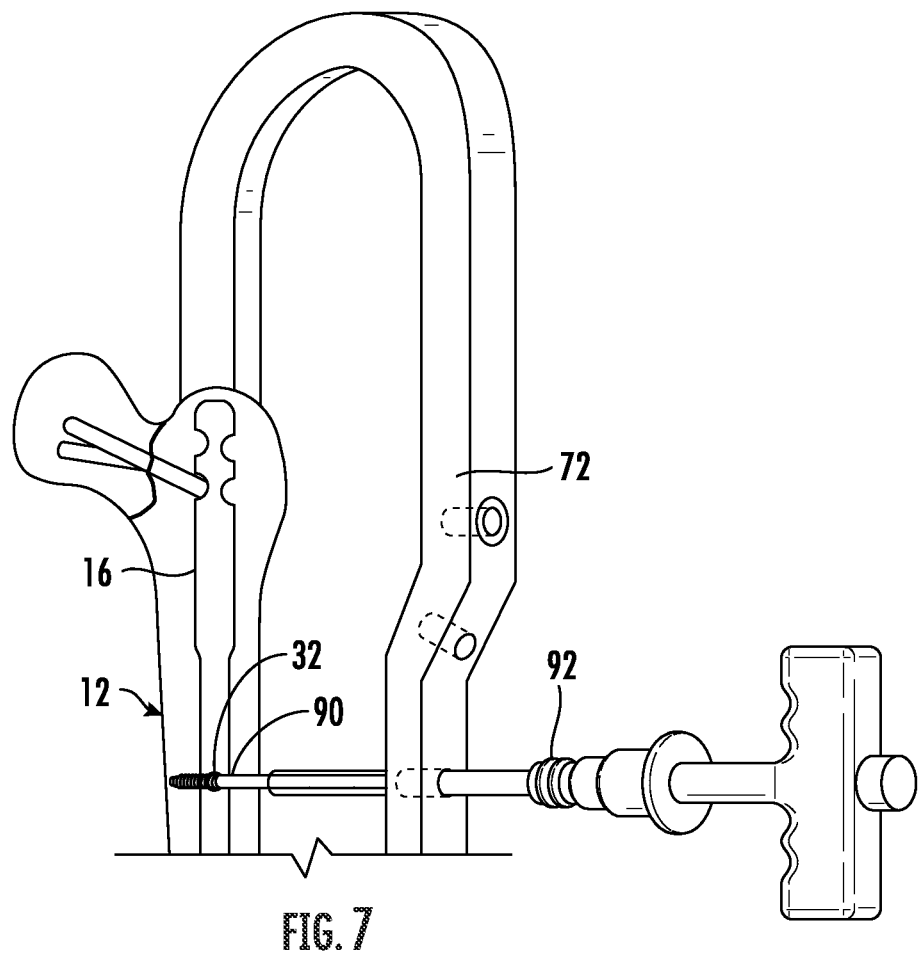
FIG. 7 shows a cortical screw being inserted in a first targeted hole in an intramedullary nail in a femur.

If distal locking is necessary, a first cortical screw passageway 90 can be drilled in the femur, at a location aligned with the first targeted screw hole 32 in the distal portion of the intramedullary nail 16, and a cortical screw can be inserted in the first screw passageway 90 using a hex driver 92 that passes through the proximal cortical screw targeting bore 80 in the targeting arm 72, as shown in FIG. 7.

Figure 8:
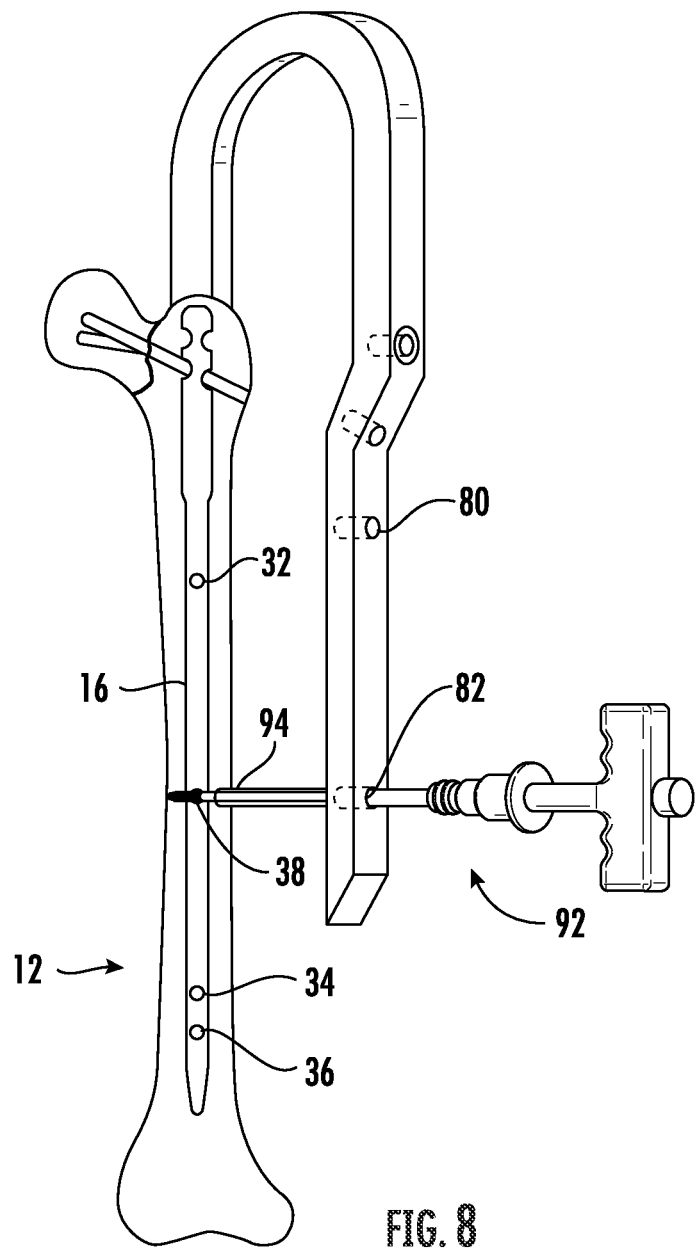
FIG. 8 shows a cortical screw being inserted in a second targeted hole in an intramedullary nail in a femur.

Instead of, or in addition to, using the first targeted screw hole 32 to create a distal lock, the surgeon may choose to use the second targeted screw hole 38, as shown in FIG. 8. This is accomplished by drilling a second cortical screw passageway 94 in the femur 12, at a location aligned with the second targeted screw hole 38 in the distal portion of the intramedullary nail 16, and inserting a cortical screw in the second cortical screw passageway 94 using the hex driver 92, which passes through the distal cortical screw targeting bore 82 in the targeting arm 72.

Instead of, or in addition to using the first and/or second targeted screw holes 32, 38 to create the distal lock, the surgeon may also use conventional methods to insert cortical screws through the distal locking hole 34 and/or a distal locking slot 36, depending on the circumstances.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A bone fixation system comprising:
   an intramedullary nail including a proximal portion defining
      a first proximal bore configured to accept a lag screw, and
      a second proximal bore configured to accept a portion of an antirotation screw insertion tool, the second proximal bore having a predetermined diameter;
   a lag screw configured to extend through the first proximal bore in the proximal portion of the intramedullary nail, the lag screw including
      a sheath, and
      a rod mounted for sliding movement within the sheath, the rod including a threaded distal end defining an internally threaded diagonal bore having a predetermined diameter; and
   an antirotation screw configured to be mounted at the end of the antirotation screw insertion tool and inserted through the second proximal bore, the antirotation screw including
      a screw head having a predetermined diameter less than the predetermined diameter of the second proximal bore and greater than the predetermined diameter of the diagonal bore,
      a shank having a threaded distal portion configured to achieve good purchase in bone and a threaded proximal portion configured to engage the internally threaded bore of the rod.

2. The bone fixation system according to claim 1, wherein;
   the intramedullary nail has a distal portion of the intramedullary nail having a longitudinal axis;
   the first proximal bore extends at an angle in the range of about 120° to about 140° with respect to the longitudinal axis of the distal portion of the intramedullary nail; and
   the second proximal bore extends at an angle in the range of about 90° and about 105° with respect to the longitudinal axis of the distal portion of the intramedullary nail.

3. The bone fixation system according to claim 2, wherein:
   the rod has a longitudinal axis; and
   the diagonal bore extends at an angle in the range of about 25° to about 55° with respect to the longitudinal axis of the rod.

4. The bone fixation system according to claim 1, wherein:
   the sheath of the lag screw has a predetermined outer diameter; and
   the antirotation screw has a predetermined diameter not more than half the predetermined outer diameter of the sheath of the lag screw.

5. The bone fixation system according to claim 1, wherein:
   the lag screw has a predetermined length when fully extended; and
   the antirotation screw has a predetermined length no more than ¾ths of the predetermined length of the lag screw.

6. The bone fixation system according to claim 1, wherein:
   the intramedullary nail has a proximal end, a distal portion, and a predetermined length; and
   the distal portion of the intramedullary nail defines a targeted screw hole located a predetermined distance from the proximal end of the intramedullary nail, wherein the predetermined distance is between about 44% and about 67% of the predetermined length of the nail.

7. The bone fixation system according to claim 1, wherein:
   the intramedullary nail has a proximal end, a distal portion having a distal tip, and a predetermined length; and
   the distal portion of the intramedullary nail defines
      a first targeted screw hole located a first predetermined distance away from the proximal end of the intramedullary nail, wherein the first predetermined distance is between about 34% and about 52% of the predetermined length of the intramedullary nail;
      a distal locking hole located near the distal tip of the intramedullary nail;
      a distal locking slot located in close proximity to the distal locking hole; and
      a second targeted screw hole located between the first targeted screw hole and the distal locking hole.

8. A method of repairing a fracture in a femur, the method comprising;
   implanting an intramedullary nail in the femur, the intramedullary nail including
      a proximal portion defining
         a first proximal bore configured to accept a lag screw, and
         a second proximal bore configured to accept a portion of an antirotation screw insertion tool, the second proximal bore having a predetermined diameter,
      a lag screw configured to extend through the first proximal bore in the proximal portion of the intramedullary nail, the lag screw including
         a sheath, and
         a rod mounted for sliding movement within the sheath, the rod including a threaded distal end defining an internally threaded diagonal having a predetermined diameter, and
      an antirotation screw configured to be mounted at the end of the antirotation screw insertion tool and inserted through the second proximal bore, the antirotation screw including
         a screw head,
         a shank, and a locking mechanism configured to lock the antirotation screw within the diagonal bore;

inserting the lag screw through the first proximal bore in the proximal portion of the intramedullary nail;

mounting the antirotation screw on the portion of the antirotation screw insertion tool;

inserting the antirotation screw insertion tool through the second proximal bore in the proximal portion of the intramedullary nail until the screw head abuts the intramedullary nail;

manipulating the antirotation screw insertion tool to lock the antirotation screw within the diagonal bore of the lag screw; and removing the antirotation screw insertion tool.

9. The bone fixation system according to claim, 8 wherein:

the antirotation screw comprises
- a threaded distal end configured to achieve good purchase in bone; and
- a threaded proximal end; and the diagonal bore has an internally threaded end configured to mate with the threaded proximal end of the antirotation screw; and the locking mechanism comprises the threaded proximal end of the antirotation screw and the internally threaded end of the diagonal bore.

10. The method according to claim 9, wherein manipulating the antirotation screw insertion tool comprises rotating the antirotation screw until the threaded proximal end of the antirotation screw engages the internally threaded end of the diagonal bore.

* * * * *